(12) United States Patent
Singh

(10) Patent No.: US 7,319,737 B2
(45) Date of Patent: Jan. 15, 2008

(54) LAMINOGRAPHIC SYSTEM FOR 3D IMAGING AND INSPECTION

(76) Inventor: Satpal Singh, 10704 Morning Field Dr., Potomac, MD (US) 20854

( * ) Notice: Subject to any disclaimer, the term of this patent is extended or adjusted under 35 U.S.C. 154(b) by 0 days.

(21) Appl. No.: 11/399,443

(22) Filed: Apr. 7, 2006

(65) Prior Publication Data

US 2007/0237293 A1    Oct. 11, 2007

(51) Int. Cl.
*G01N 23/04* (2006.01)

(52) U.S. Cl. .......................................... 378/57

(58) Field of Classification Search .................. 378/4, 378/10, 19–26, 50–54, 57, 58, 208
See application file for complete search history.

(56) References Cited

U.S. PATENT DOCUMENTS

| | | |
|---|---|---|
| 5,182,764 A | 1/1993 | Peschmann et al. |
| 5,367,552 A * | 11/1994 | Peschmann ................. 378/57 |
| 5,583,904 A | 12/1996 | Adams |
| 5,796,802 A | 8/1998 | Gordon |
| 5,818,897 A | 10/1998 | Gordon |
| 6,088,423 A * | 7/2000 | Krug et al. .................... 378/57 |
| 6,925,141 B2 | 8/2005 | Bruder et al. |
| 6,940,942 B2 | 9/2005 | Ullberg |
| 6,993,111 B1 * | 1/2006 | Annis ........................... 378/57 |
| 7,106,830 B2 * | 9/2006 | Rosner ....................... 378/146 |
| 7,215,737 B2 * | 5/2007 | Li et al. ....................... 378/57 |
| 7,221,732 B1 * | 5/2007 | Annis ........................... 378/57 |

* cited by examiner

*Primary Examiner*—Edward J. Glick
*Assistant Examiner*—Irakli Kiknadze

(57) ABSTRACT

A digital Laminographic or Tomosynthesis method is described for use in the detection of explosives concealed in baggage. The method uses at least one source of x-ray and at least two sets of detectors, preferably more to generate 3D images of high detail. The data from the detectors can be simply time delayed and summed up to generate high definition image of layers through the bag. This leads to very high speed of 3D imaging, the same speed as in regular x-ray scanners. In addition, there is no rotating gantry, the systems is simple, compact, relatively inexpensive, and can be used to generate 3D images of large shipping containers.

13 Claims, 6 Drawing Sheets

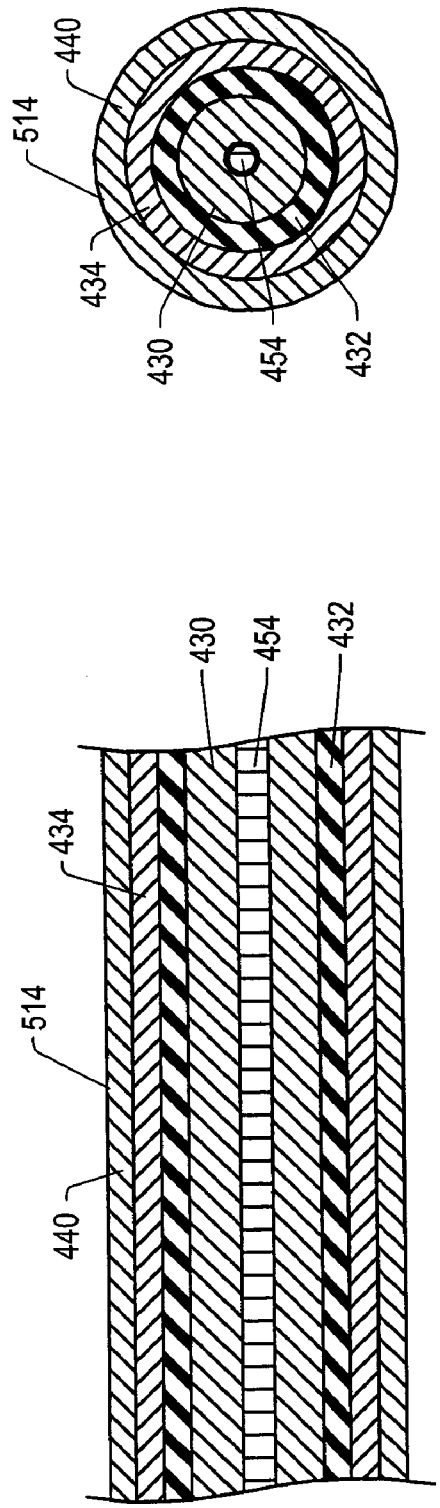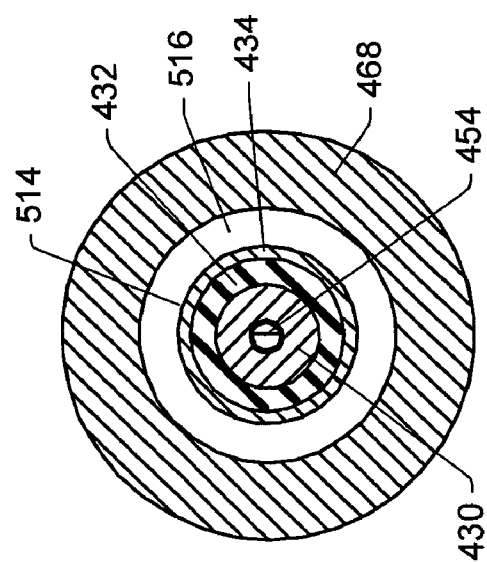

LAMINOGRAPHIC SYSTEM FOR 3D IMAGING AND INSPECTION

BACKGROUND OF THE INVENTION

1. Field of the Invention

This invention relates to the use of digital Laminography for 3D imaging and inspection of baggage or objects, the technique of Laminography is also described alternatively as Tomosynthesis or Computed Tomography from limited projections. This invention is suited for automated systems used for the detection of explosives in baggage, and for 3D imaging for medical and non-medical applications.

2. Description of the Related Art

Most of the baggage screeners in use today generate a shadow image by interposing a baggage between a x-ray source and a linear array of radiation detectors, and translating or scanning the baggage over the said linear detector. This method generates a 2 D image from which it is difficult to detect for explosive and more so if the explosives are disposed off in the form of thin sheets, this problem is well known to the people skilled in the field.

To overcome the above drawback, Computed Tomography (CT) technique has been employed which can generate cross sectional images of slices through the object. Then from several such slice images, a 3D image can be built up from which the presence of explosives within the baggage can be inferred. However, since CT is a very time consuming technique, prescanning is employed to select only certain areas of baggage for scanning, for example as explained in U.S. Pat. No. 5,182,764 (Peschmann, et al.); U.S. Pat. No. 5,367,552 (Peschmann). The CT scanners described in these patents take 0.6 to 2 secs per rotation of the gantry required to generate one cross sectional or slice image through the object. If a bag is assumed to be 70 cm long, then for a desired throughput rate of 300 bags per hour, then there is only enough time to generate images of only 6-7 slices through the bag, this is obviously highly inadequate for a reliable inspection of the bag. To speed up the scan time and to enhance the performance, multi row detectors have been used as described in U.S. Pat. No. 5,818,897 (Gordon); U.S. Pat. No. 5,796,802 (Gordon) and U.S. Pat. No. 6,925,141 B2 (Bruder, et al.). However, all the CT based systems have major drawbacks in that the throughput is slow, they do not scan the entire baggage, only select areas are scanned to reduce the scan time, are very bulky, are very complex systems with rotating gantry and are very costly with each system costing around a million dollars or more. Further, the human eye is not accustomed to seeing the contents of bags in vertical slices or layers, it would be far better if horizontal layers were displayed in case visual inspection was required. However to generate horizontal layers, the CT of the entire bag would be required with the distance between slices kept very small requiring hundreds of slices to be taken which would take a very long time.

Another problem with the CT based techniques is that the systems are very bulky and complex, and it would be almost unthinkable to build one such system to generate a 3D image of large shipping containers or trucks. CT requires a rotating gantry around the object, to build such a massive gantry that rotates around a large shipping container at high speed and at a uniform rate without introducing too much vibrations that would otherwise corrupt the data, is a task so daunting that no one has ever built such a system. There are at present no systems available to build a 3D image of large shipping containers or trucks or cars.

A different approach from the CT methods of above has been described in the U.S. Pat. No. 6,088,423 (Krug, et al.) wherein 3 x-ray tubes and 3 sets of "L" shaped linear detectors are used for baggage screening, this method has been described as the Multi view Tomography. However, as is well known to one skilled in the art of CT, just 3 projections obtained are not enough to build a detailed 3D image of the object, and this technique therefore leaves to question the full efficacy of the technique. Further, the method using three x-ray tubes, is also very costly, bulky and has therefore found only limited use a airports and not suited for wide use as the ordinary x-ray scanners.

The above methods of CT, and the multiview Tomography do not generate high detail 3D images at high speeds. These methods have failed to take advantage of the fact that most bags are rather flat. Also these methods have not focused on generating slice images of horizontal layers within a bag which a human eye would find easier to decipher.

The methods of Laminography, more recently termed as Tomosynthesis, are good for generating slice images that are horizontal and can be suitable for imaging of the bags. The traditional methods of Laminography employed films and that made it almost impossible to use them for baggage screening. In recent times, Laminography has been used for inspection and imaging, but on a limited scale.

A high speed Laminography or tomosynthesis method using at least two linear detector arrays and at least one x-ray source, though the preferred embodiment uses four linear array detectors and two x-ray sources has been described in U.S. Pat. No. 5,583,904 (Adams). This method has been shown good for the inspection of thin objects like Printed Circuit Boards used in the electronic industry. This patent does not address the issue of explosive detection within a baggage.

A system very similar to the above, using one x-ray source and a stack of two or more linear detectors has been described in U.S. Pat. No. 6,940,942 B2. The system presented therein has been described for use in medical imaging and does not address the issue of explosive detection in baggage.

OBJECTS OF THE INVENTION

It is, accordingly, an object of the invention to provide a high speed baggage inspection system for the detection of explosives concealed in a bag.

Another object of the invention is to provide a 3D image in high detail of the object being investigated.

Another object of this invention is to generate horizontal slice images of a bag which the human eye is more accustomed to seeing and deciphering than vertical slices produced by conventional CT systems.

Another object of the invention is to provide a low cost and more compact system compared to the existing explosive detection systems used for baggage screening.

Yet another object of the invention is to provide a method for generating 3D images of large shipping containers, trucks, motor vehicles and other large sized objects for which there is no system as yet in the market available.

These and other objects will become apparent in the description that follows.

SUMMARY OF THE INVENTION

This method describes a method of generating 3D images of high detail at high speed for use for package inspection, detection of explosives and contraband concealed in baggage, and for medical applications. The existing 3D methods employed for baggage screening use the methods of Computed Tomography (CT) which are very slow, very costly, very bulky. The CT methods typically use a complex rotating gantry, generate a sectional slice image of the object in 0.5 to 2 secs typically, and that leaves time for only 6 to 7 scans for a bag that is 70 cm long and is scanned at a speed of 25 cm/sec as in most x-ray scanners. The use of pres-canning by conventional x-ray scanners that generate 2D images is employed to selectively CT scan only certain areas of the bag, but this is not the desired or optimal way. Further, it would be unthinkable of building such a giant gantry that goes around large shipping containers or trucks to generate a 3D image for inspection.

The invention described herein, overcomes the above problem by employing the method of Laminography, also referred to as Tomosynthesis, to generate high definition 3D images at very high speeds that are used in conventional x-ray scanners that generate 2D images. The system is relatively inexpensive, compact and simple to operate.

The method described, involves translating the object or package relative to a x-ray radiation beam from one or more sources, and uses two or more sets of detectors, though a larger number of detector sets would be preferred to generate higher definition images.

In one embodiment of the invention, the object or bag to be scanned is placed on a conveyor belt that moves through a tunnel which houses the x-ray source and detectors. The radiation from a x-ray source is shaped by a collimator into several radiation beams that are flat and fan shaped. Each such fan beam propagates across the tunnel and is received by it associated set of detectors, the detectors are "L" shaped linear arrays. The orientation of the fan beams is such that they diverge outwards from the x-ray source and when the object is translated through the tunnel, it gets scanned at different angles by these several radiation beams. The scanned images produced by each set of detectors associated with their respective fan beams, is then time delayed to generate images of horizontal layers or slices through the object. By varying the time delays, images of horizontal layers at different heights can be quickly generated. These images then can then be analyzed by computer to identify contiguous regions of uniform or similar density, their volume estimated and mass calculated to make a determination if explosive is present or not. In addition to the mass and volume estimates, techniques of pattern extraction, pattern and texture analysis, etc can be employed to further improve the detection criteria.

In another embodiment of the invention, dual energy x-rays can be used, or dual energy detectors that are sensitive to different energy bands within the transmitted x-ray radiation are used. The use of dual or multi spectral images is considered useful for determining the mass, the density, the atomic number in order to make a determination if explosives are present.

These and several other embodiments, objects and advantages will be apparent to one skilled in the art. The description herein should be considered illustrative only and not limiting or restricting the scope of invention, the scope being indicated by the claims.

BRIEF DESCRIPTION OF THE DRAWINGS

FIG. 2 shows the end view of system in FIG. 1 and further illustrates the relative position of the x-ray source, the detectors and the bag on a conveyor belt.

DETAILED DESCRIPTION OF THE PREFERRED EMBODIMENTS

In describing the preferred embodiment and its alternatives, specific terminology will be used for the sake of clarity. However, the invention is not limited to the specific terms so used, and it should be understood that each specific term includes all its technical equivalents which operate in a similar manner to accomplish similar purpose.

Figure 1:
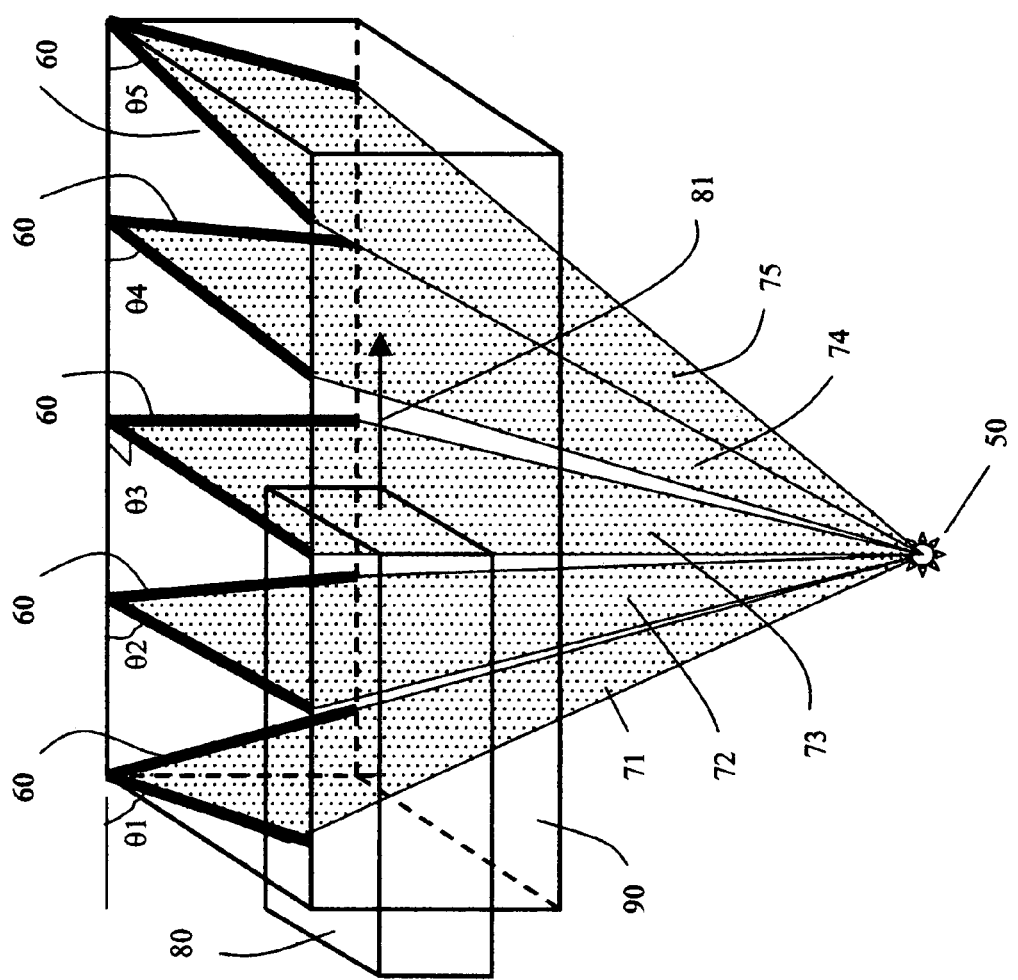
FIG. 1 shows the simplified view of one embodiment of the invention wherein a bag is transported through a tunnel such that it intercepts radiation form an x-ray source to a set of detectors.

FIG. 1 shows a preferred embodiment of the present invention as used for baggage screening. For the sake of clarity in the drawings, the ordinary details relating to the mechanics of the system have been omitted as these are well known to a person skilled in the field.

As shown in FIG. 1, an object or bag 80 is transported through a tunnel 90 in the direction of the arrow 81. Not shown in this figure to avoid the clutter are the conveyor belt, the motors and the transport mechanism and other details which are well known to a person skilled in the field.

As illustrated in FIG. 1, when the object moves through the tunnel 90, it intercepts radiation from a x-ray source 50 and going towards a set of detectors 60. The detectors are "L" shaped linear arrays, each array composed of numerous small detectors often referred to as pixels. These detectors can be of any of the several types that are well known. Not shown in this figure are the electronics that senses, amplifies, digitizes and processes the signal coming from the detectors and ships the data to a computer for further processing and display. Again, for the sake of clarity, ordinary details of a data storage memory, computer, display, High Voltage generator and control for the X-ray tube have been omitted.

The relative positions of the x-ray source 50, the bag 80, and detectors 60 are illustrated in the end view shown in FIG. 2. As shown in FIGS. 1 and 2, each of the detectors 60 is like "L" shaped and has two parts, the horizontal or the first part is shown as 601 in FIG. 2 and is on the top side of the tunnel 90, the vertical part, 602, is on the vertical or the second side of the tunnel 90. It should be noted that the detector parts 601 and 602 as shown in FIG. 2 are essentially orthogonal to each other, but need not necessarily be so. Further, each of the detector parts 601 and 602 comprises of an array of small or elemental detectors, often referred to as pixels of the detector, each of these detector elements or pixels within each of the said arrays are oriented so as to receive radiation coming from the source 50. With reference to FIG. 2, the radiation emitted from the x-ray source 50 is a cone with a beam axis 731. The dotted line 732 is perpendicular to the beam axis 731 and represents the orientation of an imaginary plane of image reconstruction, the plane being parallel to this line 732 and perpendicular to the plane of paper. The radiation 73 is shaped by a collimator 82 and passes through the object 80 transported by the conveyor belt 91.

With reference to FIG. 1, five detectors 60, have been shown for clarity, though many more could be used to generate higher definition image, and as few as two may be used where high definition is not needed or where the object 80 is very thin. Also shown in FIG. 1 are five fan beams, 71, 72, 73, 74 and 75, these fan beams are shaped by a collimator not shown in FIG. 1, but shown by its end view 82 in FIG. 2, the art of collimator use is well known in the field of x-ray imaging and it will not be discussed any further in here.

It should be noted with reference to FIG. 1, and keeping in mind the off center position of x-ray source 50 illustrated in FIG. 2, that the detectors 60 are not parallel, but make angles, θ1, θ2, θ3, θ4 and θ5, so that they are oriented so as to receive their respective fan beams, 71, 72, 73, 74 and 75. As shown in FIG. 2, the position of the x-ray source 50 is not at the center of and below the tunnel 90, but is off to one side. This allows the radiation to intercept the bag 80 at an angle as is usually done in ordinary baggage scanners.

An alternative embodiment of the invention is shown by its end view in FIG. 3 wherein the x-ray source is at the center and below the tunnel 90. This arrangement allows the use of straight linear detector array 601 at just the top of the tunnel 90. However, in this approach, the extent of detector 601 is larger compared to that in FIG. 2, and this can make the overall width of the housing of the tunnel very large, though it might be suitable for scanning of smaller sized and thinner objects.

Figure 3:
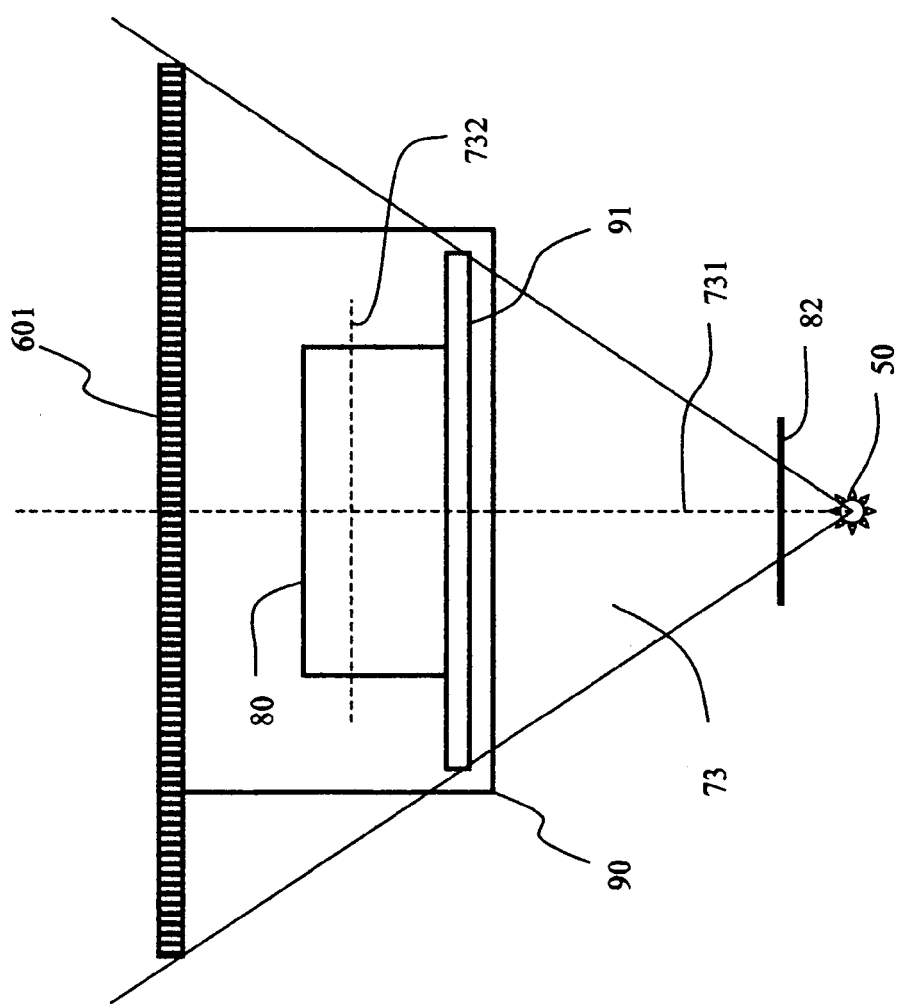
FIG. 3 shows an alternative embodiment of the invention where the x-ray source is moved to the center and below the conveyor belt, and only straight line detectors are used rather than "L" shaped detectors shown in FIG. 1.

With reference to FIGS. 1, 2 and 3, it should be noted that there are several positions and orientations of the x-ray source and its radiation possible.

Figure 5:
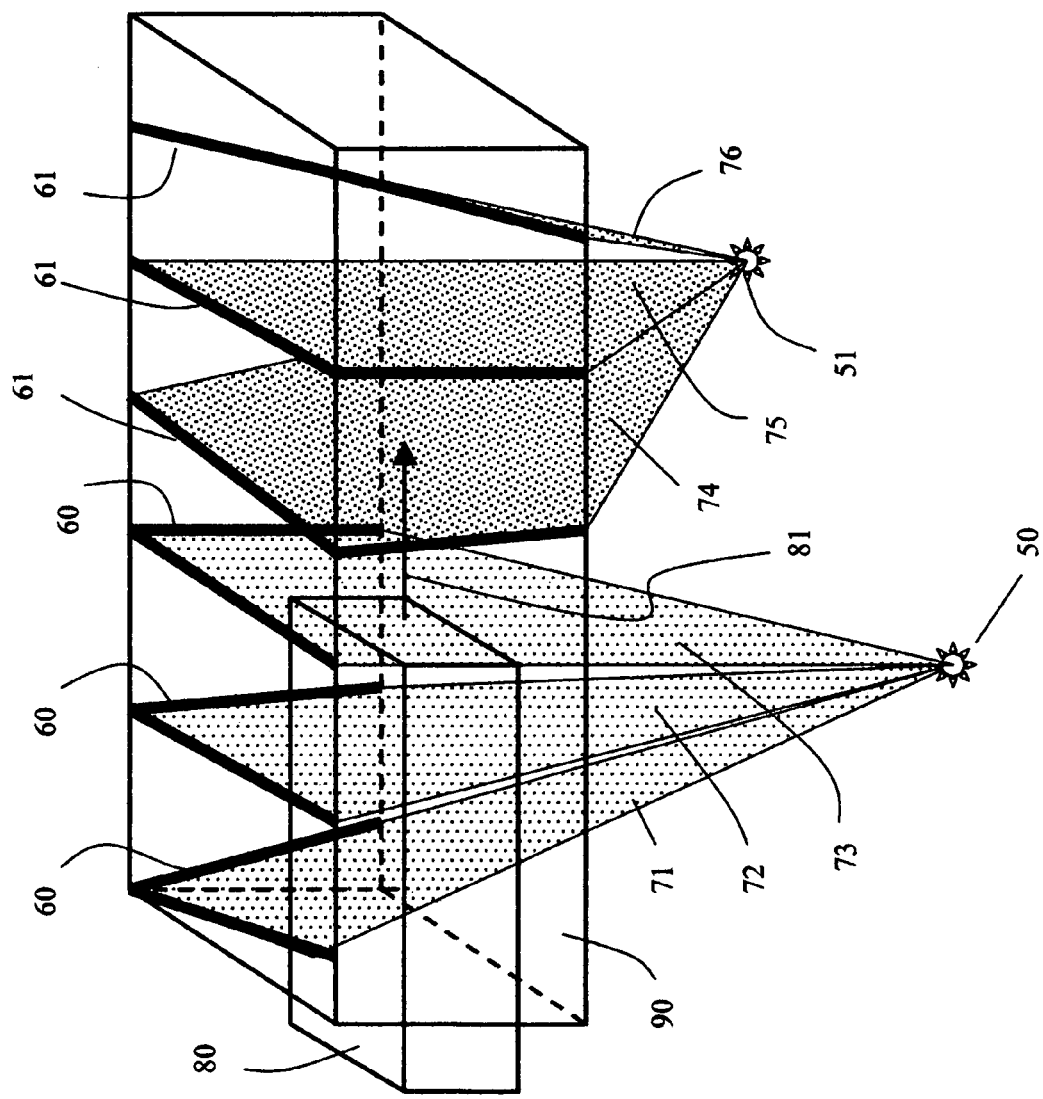
FIG. 5 shows an alternative embodiment of the invention with two x-ray sources and two sets of detectors to generate higher definition image.

Yet another embodiment of the invention is shown in FIG. 5, wherein two x-ray sources 50 and 51 are shown with their associated fan beams 71, 72, 73, and 74, 75, 76, and their respective detectors 60 and 61. The two x-ray sources, 50 and 51 would ordinarily be placed such that beam axes are at 90 degrees or some suitably large angle so that the object 80 can be viewed from wider angles, this is preferred as it leads to higher definition image. Also, only six detector sets in total have been shown in FIG. 5 for the sake of clarity, and lot more can be used. Further, as few as one detector set can be used for each x-ray source.

Figure 6:
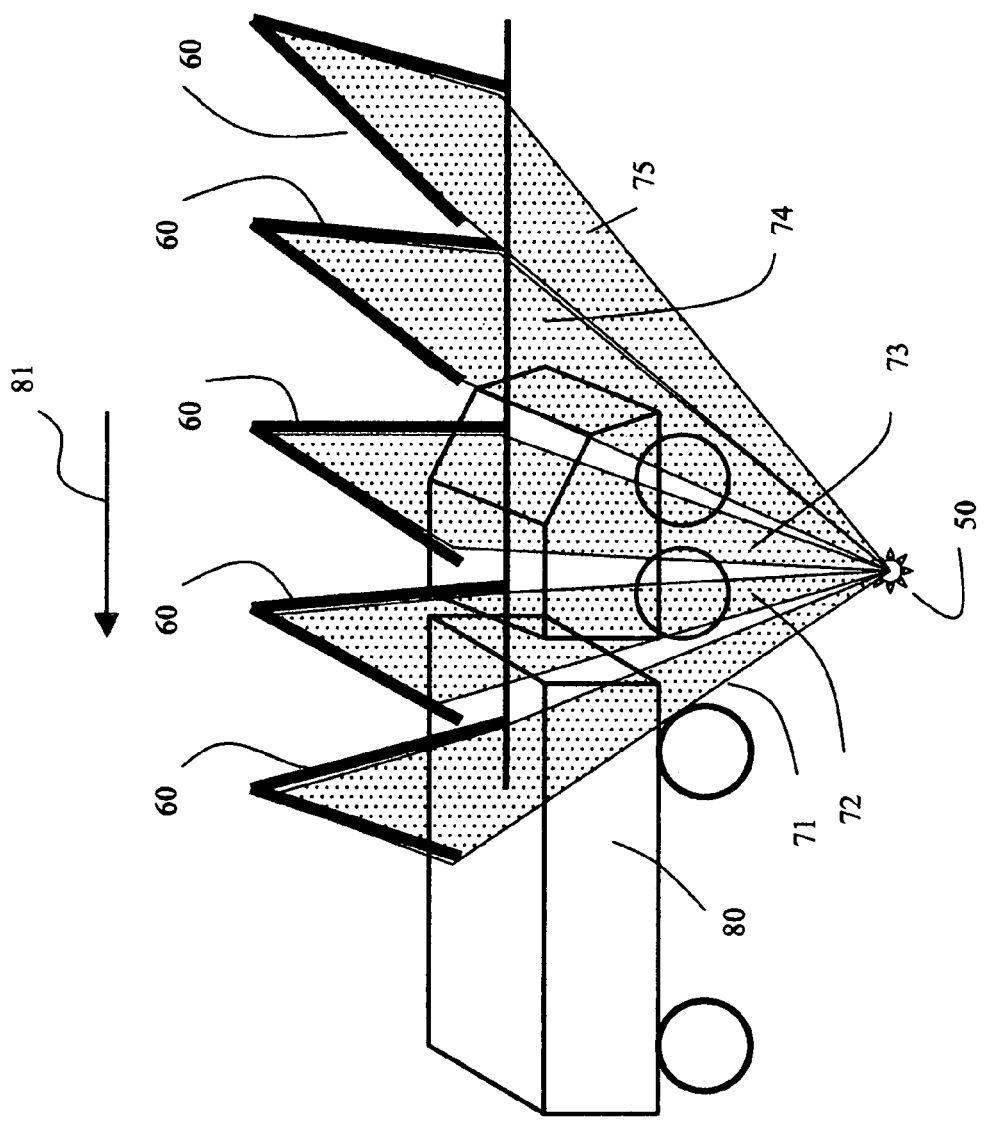
FIG. 6 shows an alternative embodiment used for inspection of large sized objects like shipping containers and trucks.

Yet another embodiment of the invention is shown in FIG. 6 for inspection of large oversized object like shipping container or a truck 80. Shown are five detectors 60 positioned to receive their respective radiation fan beams 71, 72, 73, 74 and 75 coming from a x-ray source 50. Not shown are the mechanical and electrical details of housing and operating such a system which are common knowledge. In the embodiment shown, the set of detectors 60 and the x-ray source 50 are moved in synchronous in the direction of arrow 81 to implement a scan from which 3D image of the truck 80 can be generated.

In another embodiment of the invention, dual energy x-rays are used, or dual energy detectors that are sensitive to different energy bands within the transmitted x-ray radiation are used. The information in the dual or multi spectral images is used for determining the mass, the density, the atomic number in order to make a determination if explosives are present, the use of dual energy x-rays is well known to one skilled in the art and has been the subject of several earlier patents for detection of explosives.

In yet another embodiment of the invention, several radiation or x-ray sources are used and the detectors are positioned such that each detector receives radiation from only one radiation source, however, the radiation paths between the various sources and their respective detectors are oriented differently so as to intercept the object 80 from different angles.

Laminographic Image Formation

The art of Laminography for generating cross sectional images of layers through an object have been described in U.S. Pat. No. 5,583,904 (Adams), U.S. Pat. No. 3,818,220 (Richards) and U.S. Pat. No. 3,499,146 (Richards). Laminography can also be considered as a subset of Computed Tomography (CT) used for image reconstructions from limited projections. The method of back projection for generating laminar images can be very easily accomplished as described next with reference to FIGS. 3 and 4.

Figure 4:
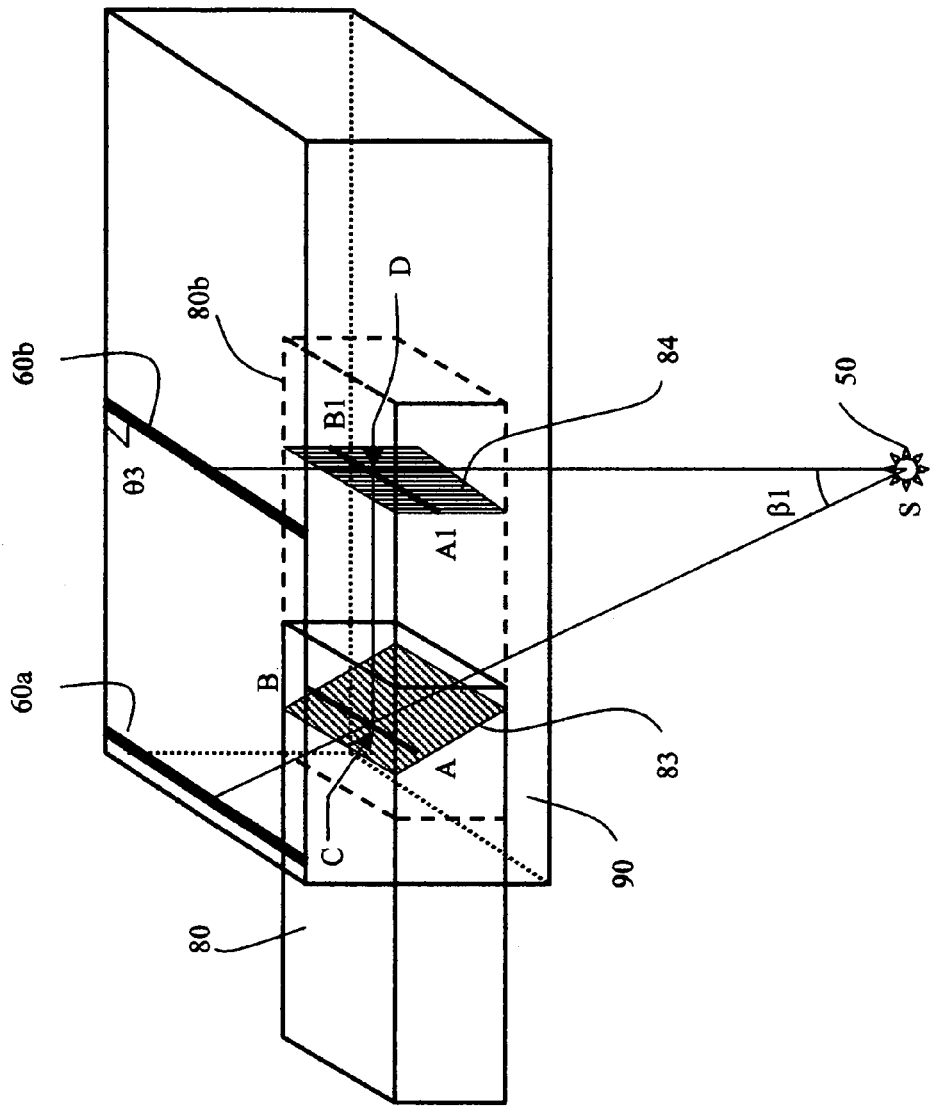
FIG. 4 illustrates with respect to line AB the process of reconstruction of image by the method of time delay and summing.

In FIG. 4 is illustrated the method for image reconstruction of a line AB within the object 80 for the embodiment shown in FIG. 3. The object 80 is shown entering the tunnel 90 from the left side, and after a certain time its position is indicated by the dotted outline 80*b*. At position 80 of the object, as shown in FIG. 4, the oblique plane 83 within the object is imaged or projected on to the left detector 60*a*. After a certain time delay when the object has moved to position 80*b*, the vertical plane 84 is imaged or projected on to the right detector 60*b*. Since the line "AB" on plane 83 is also present and shown as "A1B1" on plane 84, if the signals or projections from the detectors 60*a* and 60*b* are summed up, then only the signal corresponding to the line AB and A1B1 are added in phase and the signals corresponding to other locations within planes 83 and 84 add out of phase. If several such time delayed projections of line AB from several detector sets 60 are added such that the signal corresponding to line AB always add in phase, then the line AB would be in focus and signals from all other locations would be out of focus and merge into the background. This method of image reconstruction of a line is similar to the principle of Laminography and back projection which is well documented in/literature and well understood. This process of time delayed summing of projections from different detector sets provides a very easy and convenient method of generating a high resolution image of a lamination or a horizontal layer within the object 80, the cross section of such a horizontal plane is indicated by the dotted line 732 in FIG. 3. By adjusting the amount of time delay, images of horizontal layers at different heights within the object 80 can be generated.

It should be noted as is well known in the field of Laminography that more the number of projections added or used to generate an image of a layer or slice, better the resolution.

The above method of time delayed summing when applied to the embodiment of FIG. 2 which shows the beam axis 731 at an angle, the plane of the reconstructed image layer is now not horizontal, but tilted as indicated by dotted line 732.

In addition to the time delayed summing method described above, any one of other methods like Algebraic Reconstruction methods, Fourier Domain methods, Iterative methods or methods of Computed Tomography from limited projections can be applied to generate 3D image of the object under investigation.

Density Calculation and Explosive Detection

The 3D image generated by the use of x-rays as described above is a 3D profile of x-ray attenuation coefficients and also of the density of the object volume under investigation. From this 3D density profile of the bag, the size, shape, volume and mass of various objects or regions within the bag can be identified. For example, consider the object or bag being composed of small elemental volumes called voxels, then by comparing the value of each voxel to a set of its nearest neighbors to check for object continuity, the size, shape and volume of the object region within the bag can be determined. This step of object region identification within the bag can be described as identifying contiguous regions with uniform or similar densities. The mass of the object region thus determined is then computed as the product of the volume and the density information which is already available in the form of 3D image reconstructed earlier. The determination for explosives is usually made if the object region density and weight crosses a certain threshold. In addition, other criteria as shape, size, texture, feature extraction, image analysis and pattern recognition may also be used to make a final determination if the explosives are present or not. In addition, two sets of detectors can be used that are responsive to two different energy spectras of the x-ray radiation used to obtain a dual energy profile of the object under investigation, the use of dual energy data further aids the detection of explosives within a bag. The use of x-ray imaging for the detection of explosives has been described in U.S. Pat. No. 5,182,764 (Peschmann, et al.); U.S. Pat. No. 5,367,552 (Peschmann); U.S. Pat. No. 6,088,423 (Krug et. al.); U.S. Pat. No. 5,796,802 (Gordon) and U.S. Pat. No. 5,600,700 (Krug et al.); it is therefore not discussed any further.

The foregoing description of the invention and its embodiments should be considered as illustrative only of the concept and principles of the invention. The invention may be configured in a variety of ways, shapes and sizes and is not limited to the description above. Numerous applications of the present invention will readily occur to those skilled in the art, for example, the described invention can be used for medical imaging, for generating high definition images of chest and lungs for cancer detection. Therefore, it is desired that the scope of the present invention not be limited by the description above but by the claims presented herein.

The invention claimed is:

1. A method of analyzing a three dimensional volume of an object using a computer and a memory, comprising the steps of:
 generating radiation using a radiation source;
 positioning a plurality of detectors to receive said radiation from said radiation source such that each said detector receives said radiation along paths oriented at different angles with respect to each other; each said detector comprising of a first part and a second part, said plurality of detectors so arranged that none of said parts are parallel, further each said part of said detector comprises an array of small elemental or pixel detectors;
 interposing said object between said detectors and said radiation source;
 translating said object relative to said detectors and said radiation source;
 recording data repetitively from said detectors as said object is translated relative to said radiation source and said detectors;
 storing said data in memory; and
 using a computer for analyzing a three dimensional volume of said object from said data.

2. The method of claim 1 wherein translating of said object is over a translation path, and further said detectors comprise of at least two linear arrays arranged at angles with respect to said translation path such that each said linear array receives radiation from said radiation source at different angles.

3. The method of claim 2 wherein said first part and said second part are arranged such that said detectors are "L" shaped.

4. The method of claim 2 further comprising the steps of: processing said data stored in said memory by using said computer to identify contiguous regions of similar object densities.

5. The method of claim 1 wherein said first part and said second part are arranged such that said detectors are "L" shaped.

6. The method of claim 1 wherein said radiation source emits said radiation having an axis of symmetry; further, said axis of symmetry making any angle, inclusive of orthogonal and oblique, to said translation path such that said radiation is directed towards said detectors.

7. The method of claim 1 further comprising the steps of: processing said data stored in said memory by using said computer to identify contiguous regions of similar object densities.

8. An apparatus for analyzing a three dimensional volume of an object
 using a computer and a memory, further comprising of:
 a radiation source to generate radiation;
 plurality of detectors positioned to receive said radiation from said radiation source such that each said detector receives said radiation along paths oriented at different angles with respect to each other; each said detector comprising of a first part and a second part, said plurality of detectors so arranged that none of said parts are parallel further each said part of said detector comprises an array of small elemental or pixal detectors;
 means to interpose said object between said detectors and said radiation source;
 means to translate said object relative to said detectors and said radiation source;
 means to record data repetitively from said detectors as said object is translated relative to said radiation source and said detectors;
 means to store said data in memory; and
 computer for analyzing a three dimensional volume of said object from said data.

9. The apparatus of claim 8 wherein means to translate said object translates said object over a translation path, and further said detectors comprise of at least two linear arrays arranged at angles with respect to said translation path such that each said linear array receives radiation from said radiation source at different angles.

10. The apparatus of claim 9 wherein said first part and said second part are arranged such that said detectors are "L" shaped.

11. The apparatus of claim 8 wherein said first part and said second part are arranged such that said detectors are "L" shaped.

12. The apparatus of claim 8 wherein said radiation source emits said radiation having an axis of symmetry; further, said axis of symmetry makes any angle, inclusive of orthogonal and oblique, to said translation path such that said radiation is directed towards said detectors.

13. The apparatus of claim 8 wherein said data stored in said memory is processed by using said computer to identify contiguous regions of similar object densities.

* * * * *

UNITED STATES PATENT AND TRADEMARK OFFICE
CERTIFICATE OF CORRECTION

| | | |
|---|---|---|
| PATENT NO. | : 7,319,737 B2 | Page 1 of 1 |
| APPLICATION NO. | : 11/399443 | |
| DATED | : January 15, 2008 | |
| INVENTOR(S) | : Satpal Singh | |

It is certified that error appears in the above-identified patent and that said Letters Patent is hereby corrected as shown below:

Drawings
On sheet 2 of 6 of drawings, delete FIG. 66a, FIG. 66B and FIG. 67, as these figures were not a part of the application.

Signed and Sealed this

Thirteenth Day of May, 2008

JON W. DUDAS
*Director of the United States Patent and Trademark Office*